United States Patent [19]
Sawyer et al.

[11] Patent Number: 6,025,330
[45] Date of Patent: Feb. 15, 2000

[54] INHIBITORS OF FIBRIN CROSS-LINKING AND/OR TRANSGLUTAMINASES

[75] Inventors: Roy T. Sawyer, Hendy; Robert B. Wallis, Carmarthen; Lisa Seale, Swansea; Sarah Finney, Tondu, all of United Kingdom

[73] Assignee: BioPharm Research & Development Ltd., Jersey, United Kingdom

[21] Appl. No.: 08/945,998

[22] PCT Filed: May 7, 1996

[86] PCT No.: PCT/GB96/01093

§ 371 Date: May 14, 1998

§ 102(e) Date: May 14, 1998

[87] PCT Pub. No.: WO96/34890

PCT Pub. Date: Nov. 7, 1996

[30] Foreign Application Priority Data

May 5, 1995 [GB] United Kingdom .................. 9509271

[51] Int. Cl.[7] ..................................................... A61K 38/00
[52] U.S. Cl. ................................ 514/12; 514/13; 514/2; 530/324; 530/325; 530/326; 530/416; 530/417
[58] Field of Search .................... 514/12, 13, 2; 530/324, 325, 326, 416, 417

[56] References Cited

U.S. PATENT DOCUMENTS 5,114,922  5/1992  Maschler et al. .................... 514/12
5,227,469  7/1993  Lazarus et al. ...................... 530/324

*Primary Examiner*—Michael P. Woodward
*Assistant Examiner*—C. Delacroix-Muirheid
*Attorney, Agent, or Firm*—Kohn & Associates

[57] ABSTRACT

The inhibitors, obtainable from tissue or secretions of leeches typically of the order Rhynchobdellida, has the following terminal sequence: $NH_2$-Lys-Leu-Leu-Pro-Cys-Lys-Glu-Y-His-Gln-Gly-Ile-Pro-Asn-Pro-Arg- wherein Y represents any amino acid sequence; or a pharmaceutically acceptable salt, derivative or bioprecursor of said sequence, or an analogue or homologue thereof. Because of their extreme potency in the nanomolar range, they can be used to treat a number of diseases where protein cross-linking is important. They can be used for the treatment of Crohn's disease, tumor implantation, atherosclerosis, thrombotic microangiopathy, fibrous growths of the skin, acne, scar formation, membranous glomerulonephrits, cataracts, or infection with microfilarial nematodes. In particular, they can be used to reduce the stability of thrombi so that they are more susceptible to lysis by thrombolytic agents.

20 Claims, 5 Drawing Sheets

----- = 0% lysis, ----- = 100% lysis, ——— = cross-linked fibrin control,
— — — = Tridegin (2.6 U/ml).

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 16 amino acids
      (B) TYPE: amino acid
      (C) STRANDEDNESS:
      (D) TOPOLOGY: linear    (ii) MOLECULE TYPE: peptide    (v) FRAGMENT TYPE: N-terminal    (xi) SEQUENCE DESCRIPTION: SEQ ID NO: 1:

Lys Leu Leu Pro Cys Lys Glu Xaa His Gln Gly Ile Pro Asn Pro Arg
1             5                   10                 15

(2) INFORMATION FOR SEQ ID NO: 2:

(i) SEQUENCE CHARACTERISTICS:

```
          (A) LENGTH: 66 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Peptide
          (B) LOCATION:37
          (D) OTHER INFORMATION:/product= "OTHER"
              /note= "Amino acid residue 37 represents,
              alternatively, cysteine or glutamic acid."

(ix) FEATURE:
          (A) NAME/KEY: Peptide
          (B) LOCATION:56
          (D) OTHER INFORMATION:/product= "OTHER"
              /note= "Amino acid residue 56 represents,
              alternatively, cysteine or glutamic acid."

(ix) FEATURE:
          (A) NAME/KEY: Peptide
          (B) LOCATION:66
          (D) OTHER INFORMATION:/product= "OTHER"
              /note= "Amino acid residue 66 represents,
              alternatively, cysteine or glutamic acid."

(xi) SEQUENCE DESCRIPTION: SEQ ID NO: 2:

Lys Leu Leu Pro Cys Lys Glu Xaa His Gln Gly Ile Pro Asn Pro Arg
1               5                   10                  15

Cys Xaa Cys Gly Ala Asp Leu Glu Xaa Ala Gln Asp Gln Tyr Cys Ala
            20                  25                  30

Phe Ile Pro Gln Xaa Arg Pro Arg Ser Glu Leu Ile Lys Pro Met Asp
            35                  40                  45

Asp Ile Tyr Gln Arg Pro Val Xaa Phe Pro Asn Leu Pro Leu Lys Pro
    50                  55                  60

Arg Xaa
65
```

INHIBITORS OF FIBRIN CROSS-LINKING AND/OR TRANSGLUTAMINASES

TECHNICAL FIELD

The present invention is concerned with a novel class of inhibitors of fibrin cross-linking and/or of transglutaminase activity, and in particular, with such inhibitors which may be, for example, derived from leech tissue and/or from leech secretions.

BACKGROUND OF THE INVENTION

Enzymes known as transglutaminases are primarily responsible for the stabilisation of many protein aggregates, such as for example, in blood clot formation. The cross-linking of proteins by the action of transglutaminases is the major way in which, for example, fibrin clots are stabilised. In mammals, stabilisation of blood clots is brought about by a transglutaminase, known as Factor XIIIa, which catalyses the formation of cross-linking between the fibres of fibrin. Cross-linked blood clots are not as susceptible to the action of fibrinolytic enzymes and are virtually insoluble in denaturing solvents, such as 5M urea.

Factor XIIIa is an atypical coagulation enzyme since it is not a serine protease but rather a cysteine-containing, transamidating enzyme which catalyses the reaction between the amino acid side chains of lysine and glutamine to form an amide link with the elimination of ammonia according to the following scheme;

When fibrin is the substrate, $R_1$—$CONH_2$ and $R_2$—$NH_2$ are glutamine and lysine side chains respectively in different chains of the fibrin polypeptide.

Factor XIIIa can also catalyse the cross-linking of other proteins. For example Factor XIIIa is known to link $\alpha_2$ antiplasmin to fibrin and increase resistance to fibrinolysis. Moreover it can cause cross-links between a range of disparate structural and contractile proteins such as collagen, laminin actin, myosin, thrombospondin, vinculin and vitronectin or the like. It is believed that this property is part of the wound healing process and may have a role in the pathology of a number of diseases of tissue remodelling.

It is therefore desirable to provide an inhibitor of transglutaminases which inhibitor could be used, for example, in the treatnment of various pathological or thromboembolic events. Inhibitors of translutaminases have been described previously and these generally fall into four main categories:

(a) immunoglobulins directed at the enzyme;
(b) low molecular weight substrates that compete with the natural protein substrates;
(c) reagents that react with the active site of the enzyme; and
(d) peptide fragments of Factor XIII itself.

These inhibitors are not suitable, for use in, for example, pharmaceutical formulations. for a variety of reasons, as follows:

Naturally circulating transglutaminase inhibitors have been identified previously as immunoglobulins directed at the sub-units of the transglutaminase. Such inhibitors give rise to a haemorrhagic condition caused by reduction in circulating factor XIII. U.S. Pat. No. 5,470,957 discloses using such immunoglobulins therapeutically by raising monoclonal antibodies to the transglutaminase enzyme sub-units by known techniques. A disadvantage associated with such antibodies as transglutaminase inhibitors is that they have high molecular weights and it is typically necessary to produce chimeric human analogues of the immunoglobulins before they can be used, for example, therapeutically in man.

WO91/10427 discloses transglutaminase inhibitors that are amines which act by linking to glutamine residues in one substrate to prevent cross-linking to another substrate. Such inhibitors are not very potent because they need to be present at the same concentrations as, or higher concentrations than, the natural substrate in order to have any significant inhibiting effect. Therefore they are only effective at concentrations in the region of approximately 50 μM and above.

WO92/13530 discloses using various transglutaminase inhibitors which rely on the activity of transglutaminase being largely dependent on a reactive sulfhydryl group. Therefore any reagent that alkylates or oxidises this sulfhydryl group should inhibit the activity of the transglutaminase. Such reagents are, however, very reactive and also very unstable and are therefore particularly unsuitable for use in, for example, pharmaceutical or therapeutic treatment.

Attempts to provide peptidic inhibitors which might be expected to be more specific and less toxic has so far resulted only in compounds of low potency. For example, such inhibitors are described in U.S. Pat. No. 5,328,898 and by Achyuthan K E, Slaughter T F, Santiago M A et al; in J. Biol. Chem. 268: pp. 21284–21292, 1993; "Factor XIIIa derived peptides inhibit transglutaminase activity: localisation of substrate recognition sites".

Therefore, it is the purpose of one aspect of the present invention to provide a potent inhibitor of transglutaminase enzymes and which inhibitor can be used in, for example, pharmaceutical or therapeutic use.

SUMMARY OF THE INVENTION

We have now isolated a novel polypeptide which inhibits transglutaminase activity and/or fibrin crosslinking, which polypeptide has the following amino acid sequence:

wherein $X_1$, $X_2$ and $X_3$ each represent any amino acid residue; $Z_1$, $Z_2$ and $Z_3$ each represent, simultaneously or alternatively Cys or Glu; or a pharmaceutically acceptable salt, a derivative (such as a chimeric derivative) or a bioprecursor of said amino acid sequence, or a homologue or analogue thereof of substantially similar activity. By homologue, we mean a polypeptide in which no more than 23% of the amino acids in the polypeptide chain differ from those listed. The figure of 23% is based on the fact that many homologues of hirudin occurring naturally in *Hirudo*

*medicinalis* are described in the literature; the most diverse of these differ in 15 of the 65 amino acids in the polypeptide chain. By analogue, we mean that one or more additional amino acids may be interposed in the polypeptide chain, provided that they do not significantly interfere with the pharmacological activity of the polypeptide. The invention also encompasses truncated forms of the polypeptide having the above-mentioned amino acid sequence.

The polypeptides according to the invention are highly potent inhibitors of transglutaminase activity and/or fibrin cross-linking. The ability of the polypeptides according to the invention to prevent formation of protein cross-links has a dramatic effect on the instability of, for example, blood clots. The inhibitory effect of the polypeptides according to the invention on factor XIIIa can be measured by the increased solubility of fibrin clots in 5M urea. In addition the inhibitory effect of the polypeptides may be measured by utilising the fact that the polypeptides inhibit ammonia release by incorporation of ethylamine into casein and also by incorporating biotinamidopentylamine into casein.

The amino terminal domain is believed to be a particularly potent inhibitor of transglutaminase activity. The invention therefore further comprises a polypeptide which specifically inhibits transglutaminase activity, which polypeptide comprises the following amino acid sequence:

NH$_2$-Lys-Leu-Leu-Pro-Cys-Lys-Glu-Y-His-Gln-Gly-Ile-Pro-Asn-Pro-Argwherein Y represents any amino acid residue or a pharmaceutically acceptable salt, derivative or bioprecursor thereof, or a homologue or analogue thereof of substantially similar activity (sequence ID No: 1).

The polypeptides according to the invention (which will hereinafter be referred to as the "Tridegins"), advantageously inhibit transglutaminase activity directly at concentrations in the 1–50 nanomolar range (a difference by at least a factor of 1000 relative to the known transglutaminase inhibitors of categories (b), (c) and (d) described above).

The Tridegins can advantageously form pharmaceutically acceptable salts with any suitable non toxic, organic or inorganic acid. Examples of such inorganic acids include hydrochloric, hydrobromic, sulfuric or phosphoric acid and acid metal salts such as sodium monohydrogen orthophosphate and potassium hydrosulfate. Examples of organic acids include the mono, di and tri carboxylic acids such as acetic, glycolic, lactic, pyruvic and sultonic acids or the like. Salts of the carboxy terminal amino acid moiety include the non toxic carboxylic acid salts formed with any suitable inorganic or organic bases.

The Tridegins according to the invention may be extracted from leech tissue or secretions by, for example, homogenisation of substantially the whole leech, the salivary glands or the proboscis or the like, in a suitable buffer. Transglutaminase inhibitors had not previously been identified in, or extracted from, leeches; the present invention therefore comprises an inhibitor of transglutaminase activity derivable from leech tissue or leech secretions. The term "derivable" as used herein encompasses the material which is directly derived, as well as material which is indirectly derived or converted to a chemically modified derivative.

The Tridegins according to the invention are typically extracted or purified using a combination of known techniques such as, for example, ion-exchange, gel filtration and/or reverse phase chromatography.

Leeches of the same genus, or even the same species, often have polypeptides in their saliva which have similar biochemical effects and are highly homologous in their amino acid structure. In the same species of leech, several different isoforms may exist differing by only a few amino acids.

The Tridegins according to the invention are derivable from leech tissue or leech secretions, typically from leeches of the order Rhynchobdellida. However, because many of the components of the salivary gland or tissue secretions from leeches which have similar biochemical specificity are members of such homologous families of polypeptides, the present invention also comprises such isoforms and analogues of the Tridegins according to the invention derivable from leeches. Furthermore, post-translational modification of leech polypeptides is frequently observed, and in view of the fact that some of the residues in the Tridegins could not be assigned to a known amino acid structure, the present invention also includes such post-translationally modified polypeptides corresponding to the polypeptides of the abovementioned sequences.

According to a second aspect of the present invention, there is provided an inhibitor of fibrin crosslinking and/or transglutaminase activity, which inhibitor is derivable from leech tissue or leech secretions, typically from leeches of the order Rhynchobdellida, more preferably from leeches of the genus Haementeria.

The inhibitor according to the invention preferably has an apparent molecular weight in the range between approximately 7000 daltons and 8000 daltons, as measured by polyacrylamide gel electrophoresis (PAGE), and has the ability to inhibit the factor XIIIa catalysed release of ammonia from the incorporation of amines into casein, and the factor XIIIa catalysed incorporation of biotinamidopentylamine into casein.

In addition to the effect on factor XIIIa, the Tridegins are inhibitors of many different transglutaminases as they inhibit the activity of both plasma and platelet factor XIIIa and tissue transglutaminase from guinea pig liver albeit with different potency. They are therefore also general transglutaminase inhibitors and can be expected to inhibit many different types of this group of enzymes.

The invention also comprises a diagnostic method of measuring the degree of inhibition of transglutaminase activity for an inhibitor according to the invention (as defined above), which method comprises measuring the amount of ammonia liberated from the transglutaminase catalysed incorporation of amines into casein in the presence of the inhibitor, wherein the amount of ammonia liberated and/or amine incorporation provides a measure of the level of inhibition of the transglutaminase activity by the inhibitor.

According to a further aspect of the present invention, there is provided a pharmaceutical formulation comprising an inhibitor according to the first or second aspect of the invention (as described above) and a pharmaceutically acceptable carrier, diluent or excipient therefor.

Because of the low level of toxicity and the high level of inhibition of transglutaminase activity associated with the Tridegins, they can advantageously be incorporated into pharmaceutical formulations, which formulations may be, for example, administered to a patient either parenterally or orally.

The term "parenteral" as used herein includes subcutaneous. intravenous, intraarticular and intratracheal injection and infusion techniques. Other means of administration such as oral administration or topical application may also be used. Parenteral compositions and combinations are preferably administered intravenously either in a bolus form or as a constant infusion according to known procedures.

The term "pharmaceutically acceptable carrier" as used herein should be taken to mean any inert, non toxic, solid or liquid filler, diluent or encapsulating material, which does not react adversely with the active compound or with a patient. Preferred liquid carriers which are well known, include sterile water, saline, aqueous dextrose, sugar solutions, ethanol, glycols and oils. Tablets and capsules for oral administration may contain conventional excipients such as binding agents, fillers, lubricants and wetting agents etc. Oral liquid preparations may be in the form of aqueous or oily suspensions, solutions, emulsions, syrups, elixirs or the like, or may be presented as a dry product for reconstitution with water or other suitable vehicle for use.

Such liquid preparations may contain conventional additives such as suspending agents, emulsifying agents, non-aqueous vehicles and preservatives. Topical applications may be in the form of aqueous or oily suspensions, solutions, emulsions, jellies or, preferably, emulsion ointments.

Unit doses of pharmaceutical formulations according to the invention may contain daily required amounts of the Tridegin, or sub-multiples thereof to make a desired dose. The optimum therapeutically acceptable dosage and dose rate for a given patient (which may be a mammal such as a human) depend on a variety of factors, such as the activity of the specific active material employed, the age, body weight, general health, sex, diet, time and route of administration, rate of clearance, the object of the treatment, i.e. treatment or prophylaxis and the nature of the disease treated.

It is expected that systemic doses in the range 0.05 to 50 mg/kg body weight, preferably between 0.05 and 10 mg/kg and more preferably 0.1 to 1 mg/kg will be effective. According to the nature of the disease to be treated, one single dose may contain from 0.05 to 10 mg/kg body weight whether applied systemically or topically.

The Tridegins can potentially be used to inhibit the stabilisation of forming thrombi in, for example, acute coronary syndromes, venous thrombosis or strokes and thereby enhance the effect of thrombolytic therapy or indeed the natural lytic processes. In this context the inhibition of the incorporation of fibrinolysis inhibitors like $\alpha_2$-antiplasmin into fibrin clots could provide an additional benefit.

The fact that the Tridegins also inhibit other transglutaminases very potently indicates additional potential uses anywhere that transglutaminase activity causes a pathological event. Such a role for transglutaminases has been hypothesised in Crohn's disease, tumour implantation, vessel wall thickening in atherosclerotic processes, thrombotic microangiopathy in, for example, the kidneys, fibrous growths of the skin such as scleroderma, membranous glomerulonephritis, repair of retinal damage, cataracts, acne, the formation of scar tissue and infection by various filarial nematodes. Not only can the Tridegins be used for their therapeutic action against the above or related syndromes but their high potency will allow lower doses.

This possibility is illustrated very well in WO93/18760, which describes the use of impotent inhibitor putrescine to treat hypertrophic scars with a preferred dose of 50 mM. The preferred concentration of a Tridegin in a similar circumstance is 1–100 µM.

A formulation according to the second aspect of the invention may advantageously be administered in combination with an anticoagulant, a thrombolytic, fibrinolytic, or fibrinogenolytic agent, or the like, which advantageously may increase the ability of the formulation to digest or inhibit, for example, blood clots. The anti-coagulant may comprise a polypeptide such as hirudin or heparin. Hirudin is disclosed in EP 0347376 and EP 0501821 and is a generic term for a family of homologous polypeptides found in a variety of leeches which specifically and potently inhibit thrombin and subsequently inhibit blood clotting. Similarly, a fibrinolytic/fibrinogenolytic agent such as hementin may be used whose activity is in digestion of fibrinogen, rendering it unclottable. Hementin is a fibrinolytic agent found in various leech species, and is disclosed in, for example, U.S. Pat. No. 4,390,630 and WO 91/15576.

A particular effect of Tridegins is to decrease the lysis time of both platelet-free and platelet-rich human plasma clots when lysis is induced by any fibrinolytic enzyme. The combination of either tissue plasminosen activator or hementin with a Tridegin results in more rapid lysis than the Tridegin alone. Since the Tridegin has no effect on its own, this shows a synergy between the two active materials. Tridegins can be used in combination with fibrinolytic agents that directly lyse fibrin (such as hementin, plasmin or Eminase) or with plasminogen activators that act through plasmin (such as streptokinase, urokinase, staphylokinase, tissue plasminogen activator or their derivatives) or with truncated forms or hybrid molecules that possess features of two or more of these agents.

Thrombolytic agents which may be included in the formulation according to the invention may comprise one or more of tissue plasminogen activator, streptokinase, Eminase, urokinase and staphlyokinase, as well as derivatives, truncated forms and hybrids thereof. Advantageously, the formulation when comprising, in addition to the Tridegins, the anticoagulant, thrombolytic or fibrinolytic agent, markedly decreases the time taken for blood clots to be digested. Therefore, Tridegins can potentially be used to inhibit the stabilisation of forming thrombi in, for example, acute coronary syndromes, venous thrombosis, or the like, and thereby enhance the effect of thrombolytic therapy. Typically the time required for 50% lysis of fibrin clots in the presence of plasmin is approximately halved if cross-linking is inhibited with one or more of the Tridegins.

Furthermore, the time for 50% lysis of plasma clots in the presence of tissue plasminogen activator is reduced by up to 40%, and similarly that by streptokinase by an amount greater than 25%.

The term "in combination", as used throughout the specification should be taken to mean the simultaneous or sequential administration of the Tridegins, according to the invention, together with any of or all of the anticoaculant, fibrinolytic, fibrinogenolytic or thrombolytic agents.

The Tridegins according to the invention may advantageously be used for the preparation of a medicament for the treatment of thromboembolic disease. Other pathological events which may be treated using the Tridegins according to the invention include Crohn's disease, tumour implantation, vessel wall thickening in atherosclerotic processes, thrombotic microangiopathy, in for example the kidney, fibrous growths of the skin, membranous glomerulonephritis, cataracts, acne and the formation of scar tissue, as well as infections with microfilarial nematodes. Advantageously, not only should the Tridegins according to the invention be useful in therapeutic treatment or prevention of such syndromes, but the high potency of the Tridegins should permit lower doses to be used.

The present invention further comprises a polypeptide produced by a recombinant DNA technique, which polypeptide is equivalent to the polypeptide defined above; the invention further comprises a synthetic or protein-engineered equivalent to the polypeptide according to the invention.

BRIEF DESCRIPTION OF THE DRAWINGS

Exemplary processes for isolation and characterisation of the polypeptide according to the invention will now be described with reference to the accompanying drawings which are given, by way of example only, wherein.

DETAILED DESCRIPTION OF THE INVENTION

EXAMPLE 1

In a first experiment A, the proboscis, anterior and posterior salivary glands of a leech of the species *Haementeria ghilianii* were homogenised together in a Potter homogeniser in 10 mM Tris HCl, 0.85% w/v NaCl pH7.0 (1 ml), and centrifuged at 13000 rpm. The supernatant was assayed in a clot solubility assay similar to that of Tymiak, Tuttle, Kimball, Wang and Lee "A simple and rapid screen for inhibitors of factor XIIIa". J. Antibiotics 46 (1993) pp. 204–206. In a second experiment B, the proboscis, anterior and posterior salivary glands were dissected from a leech of the species *Haementeria ghilianii* and homogenised separately in 0.2 ml aliquots of the buffer. The effect was compared with extracts of the proboscis, anterior and posterior salivary glands from two leeches of the species *Haementeria officinalis* prepared in 0.2 ml buffer. The test samples (30 $\mu$l) were added to a solution of 10 mg/ml crude bovine fibrinogen which contains factor XIII (30 $\mu$l). The reaction was started by adding 6.25 units/ml bovine thrombin containing 9 mM CaCl$_2$ (40 $\mu$l). A clot formed in 15 min when 8M urea (160 $\mu$l) was added and left in contact with the clot. After 30 min, the absorbance resulting from the clot's opalescence was read at 405 nm. Lowered absorbance indicates solubility of the clot resulting from inhibition of cross-linking. Table 1 shows the inhibitory effect (absorbance at 405 nm) of the various extracts on the solubility of fibrin clots compared with iodoacetamide (a known inhibitor of factor XIIIa). The numerical values quoted in the table are absorbance at 405 nm.

TABLE 1

| Test Sample | Experiment A | Experiment B |
|---|---|---|
| Tris buffer | 0.74 | 0.83 |
| Iodoacetamide (100 $\mu$M) | 0.26 | 0.42 |
| *H. ghilianii* complete salivary complex extract | 0.29 | — |
| *H. ghilianii* anterior gland extract | — | 0.43 |
| *H. ghilianii* posterior gland extract | — | 0.43 |
| *H. ghilianii* proboscis extract | — | 0.53 |
| *H. officinalis* anterior gland extract | — | 0.64 |
| *H. officinalis* posterior gland extract | — | 0.55 |
| *H. officinalis* proboscis extract | — | 0.09 |

EXAMPLE 2

In order to confirm the presence of an inhibitor of factor XIIIa, the effect of the extracts on the ability of human factor XIIIa to catalyse the incorporation of biotinamidopentylamine into casein was measured by the microtitre plate method described by Slaughter T F, Achyuthan K E, Lai T-S and Greenberg C S. (1992). ("A microtitre plate transglutaminase assay utilizing 5-(biotinamido)pentylamine as substrate"; Anal Biochem 205: 166–171). Extracts of the proboscis, anterior and posterior salivary glands of leeches of the Haementeria species were prepared as in experiment A in Example 1. Those from *Haementeria depressa* were lyophilised. As the salivary glands are not easily removable from leeches of the species, *Hirudo medicinalis* and *Hirudinaria manillensis*, the extracts were prepared by removing the anterior one third of single leeches and homogenising in 1 ml 10 mM Tris HCl containing 0.85% NaCl. The supernatant following centrifugation at 13000 rpm was used in the assay. N,N dimethylcasein was dissolved in 0.1M Tris HCl pH8.5 by stirring at 85° C. for 30 min 2000 g for 20 min. A concentration of 10–20 mg/ml (0.2 ml) was used to coat the wells of a microtitre plate by incubation at 37° C. for 1 h. The excess casein was discarded and the wells blocked with 0.5% non fat dry milk in 0.1M Tris HCl pH8.5 for 30 min. The plate was then washed twice with 0.35 ml aliquots of the Tris buffer. Factor XIIIa was prepared from citrated human plasma by defibrinogenation by addition of solid bentonite (40 mg/ml), incubation for 10 min and centrifugation at 12000 g for 2 min. The supernatant (0.5 ml) was activated by the addition of 1000 U/ml bovine thrombin (0.05 ml) and 200 mM CaCl$_2$ (0.025 ml) and incubation at 37° C. for 15 min. The thrombin was neutralised by addition of 2000 ATU/ml hirudin (0.5 ml). Microtitre plate wells (total volume 0.2 ml) contained 5 mM CaCl$_2$, 10 mM dithiothreitol, 0.5 mM biotinamidopentylamine, test sample (0.05 ml) and of the activated plasma (0.05 ml). After incubation at 37° C. for 30 min, the liquid was discarded and the reaction stopped by two washes in 0.2M EDTA (0.35 ml each) followed by two washes with 0.1M Tris HCl pH8.5 (0.35 ml each). 0.25 mg/ml streptavidin-alkaline phosphatase was diluted 1:150 with 0.5% non fat dry milk in the Tris buffer and 0.25 ml was added to each well and incubated for 1 h at 20° C. The plate was washed once with 0.1% Triton X-100 (0.35 ml) followed by 3 washes with the Tris buffer (0.35 ml).

Bound alkaline phosphatase was measured by addition of 1 mg/ml p-nitrophenyl phosphate. 5 mM MgCl$_2$ in the Tris buffer (0.05 ml) plus Tris buffer (0.2 ml) and the absorbance measured after 30 min using a Titertek Uniskan II microtitre plate reader at 405 nm. Table 2 confirms, in a different and more sensitive assay, that the Factor XIIIa inhibitory activity (measured by the incorporation of biotinamidopentylamine into casein catalysed by human plasma factor XIIIa) is found in the salivary organs of both *Haementeria ghilianii* and *Haementeria officinalis*. Moreover, significant but low inhibitory activity is detectable in the salivary glands of *Haementeria depressa* and in the anterior portions of both *Hirudo medicinalis* and *Hirudinaria manillensis*.

TABLE 2

| Test Sample | Factor XIIIa inhibitory activity (unit/complete salivary complex or unit/leech)* |
|---|---|
| Buffer control | 0.00 |
| Haementeria ghilianii | 128.7 |
| Haementeria officinalis | 10.2 |
| Haementeria depressa | 0.5 |
| Hirudo medicinalis | 1.5 |
| Hirudinaria manillensis | 2.1 |

*1 unit is defined as double the amount of transglutaminase inhibitor required to inhibit human factor XIIIa in 1 ml normal human plasma by 50%. A pool of plasma from seven healthy donors was utilised for this standardisation.

EXAMPLE 3

Figure 1:
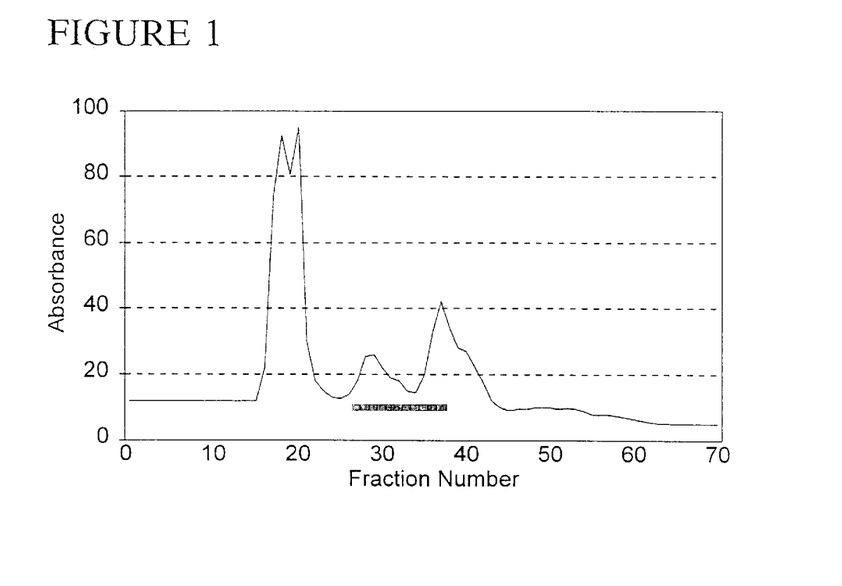
FIG. 1 is a graphic illustration of the elution of the inhibitory activity of the polypeptides according to the invention isolated according to Example 3 described below.

A homogenate was prepared in phosphate-buffered saline from five sets of the complete salivary complex (anterior, posterior glands and the proboscis) from *Haementeria ghilianii* in the same way as that described in Example 1 and the supernatant was applied to a 1.6×80 cm column of Superdex G-200 and run in phosphate-buffered saline pH7.2 at a flow rate of 1 ml/min. The eluant was monitored at 280 nm and the inhibitory activity was determined by the same assay as that described in Example 1. FIG. 1 shows the separation and the position where the inhibitory activity elutes. The bar indicates the fractions which contain the Tridegin activity.

EXAMPLE 4

A homogenate of the complete salivary complex from five *Haementeria ghilianii* was prepared in 20 mM Tris HCl pH8.0 as in Example 1. The supernatant was applied to a 0.8×7.5 cm column of Express-Ion Exchanger Q (Whatman) and eluted with a linear gradient to 20 mM Tris HCl pH8.0 containing 0.3M NaCl. The eluate was monitored by absorption at 280 nm and the Tridegin activity was determined by the clot solubility assay as in Example 1. In addition the activity of hementin was measured by a fibrinogenolytic assay and the factor Xa inhibitory activity by a chromogenic substrate assay. The hementin activity was assessed by incubating 2 mg/ml bovine fibrinogen (50 µl) with 20 mM HEPES buffer containing 10 mM $CaCl_2$ and 0.1% w/v Brij 35 pH 7.5 (25 µl) and serial dilutions of the column fractions (25 µl) at 37° C. for 60 min. Then 100 U/ml thrombin (10 µl) was added to cause clotting and the clot was measured by the turbidity at 405 nm after 30 min. Reduction in the turbidity indicated the amount of fibrinogen digested. The factor Xa chromogenic substrate assay was carried out by incubating 2 mM S2765 in 50 mM Tris HCl pH 8.3 in a spectrophotometer and measuring the rate of absorbance change at 405 nm. The reaction was started by the addition of human factor Xa.

Figure 2:
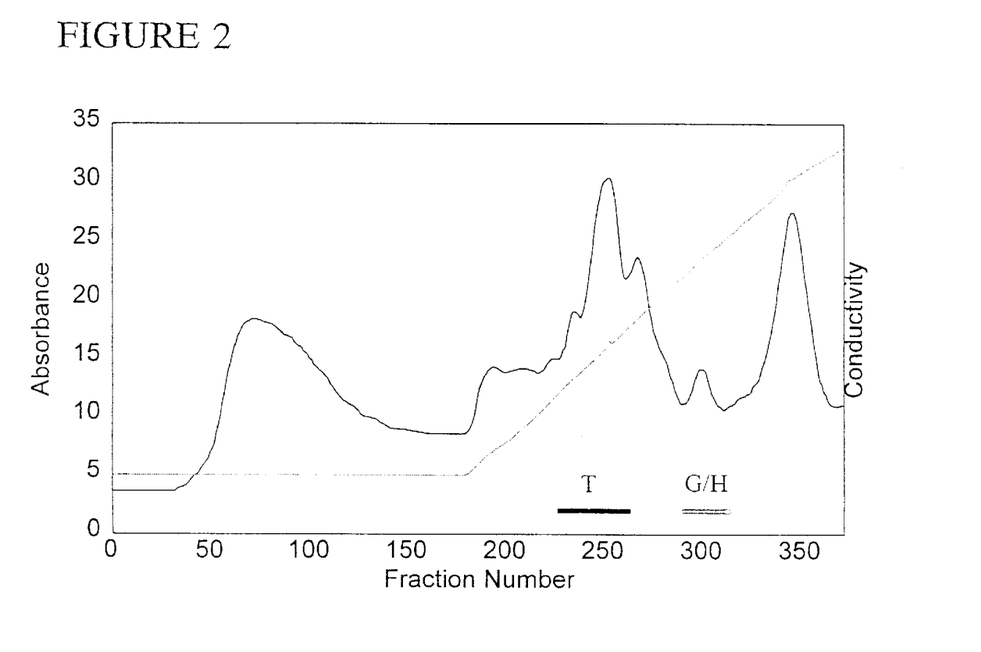
FIG. 2 is a graphic illustration of the results of Example 4 for the elution of the inhibitory activity of the polypeptide according to the invention in comparison to hementin and ghilantin.

FIG. 2 shows the elution profile on a column of SP Sepharose eluted with a linear gradient to 0.3M NaCl. The positions where the Tridegin (T), the hementin and the factor Xa inhibitory activity appears are shown; there is a very clear separation of the Tridegin from the other two salivary components, namely hementin (H) and ghilanten (G), known to be in the salivary glands of this species of leech, confirming that Tridegin differs from the known components. The fractions containing the inhibitory activity are marked with a bar and the respective letters T,G and H.

EXAMPLE 5

A homogenate of the complete salivary complex from *Haementeria ghilianii* was prepared in 20 mM ammonium formate pH3.5 (5 ml) in a similar way to that in Example 1 and applied to a 0.8×7.5 cm column of Express-Ion Exchanger S (Whatman).

Fractions were eluted with a linear salt gradient to 20 mM sodium formate containing 1M NaCl pH3.5. The eluate was monitored by absorbance at 280 nm and assayed as in Example 1. The inhibitory fraction eluted at about 0.6M.

EXAMPLE 6

Figure 3:
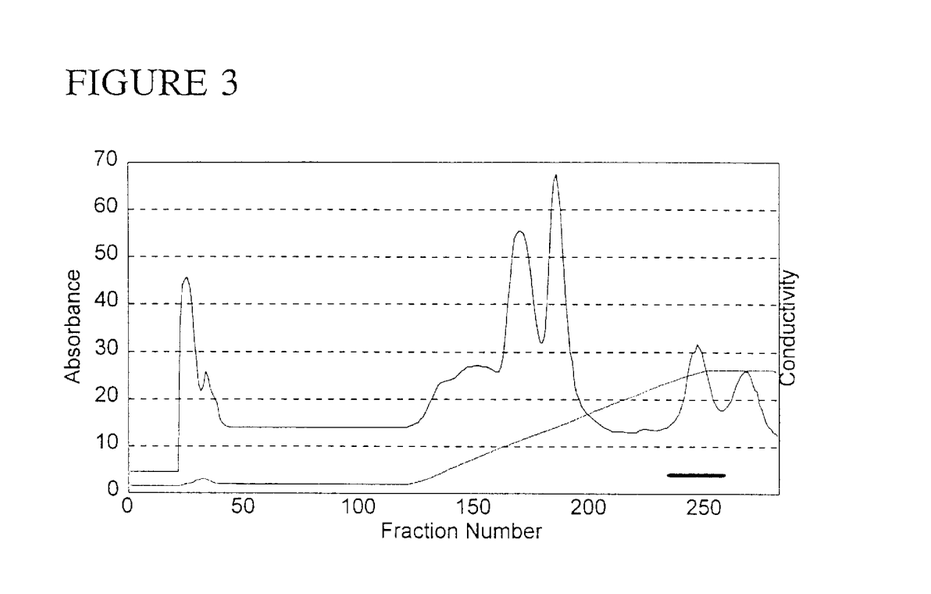
FIG. 3 is a graphic illustration of the results of Example 6 of the inhibitory activity of the polypeptide according to the invention.
Figure 4:
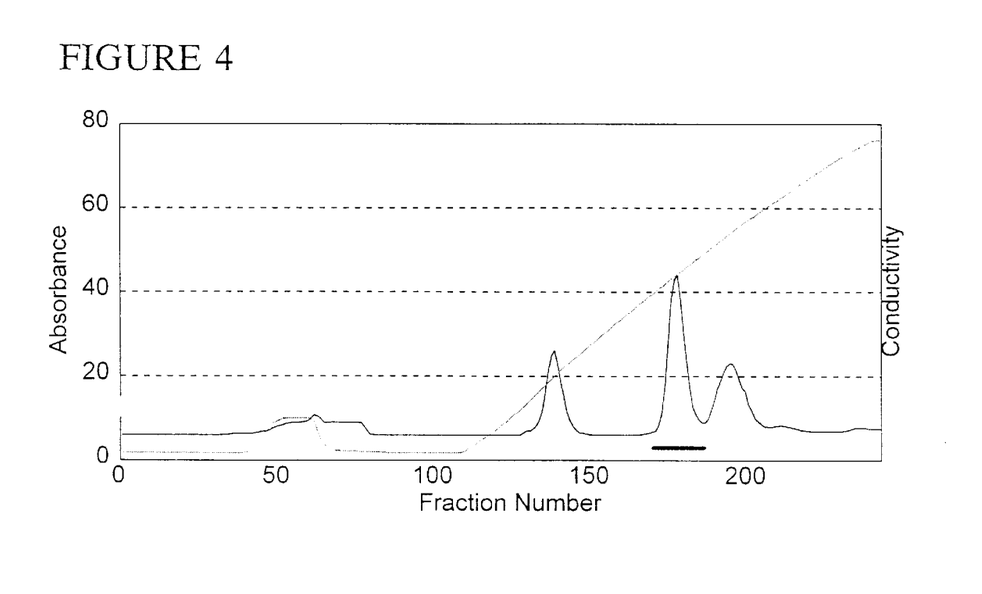
FIG. 4 is a chromatograph of the inhibitory activity from FIG. 3.
Figure 5:
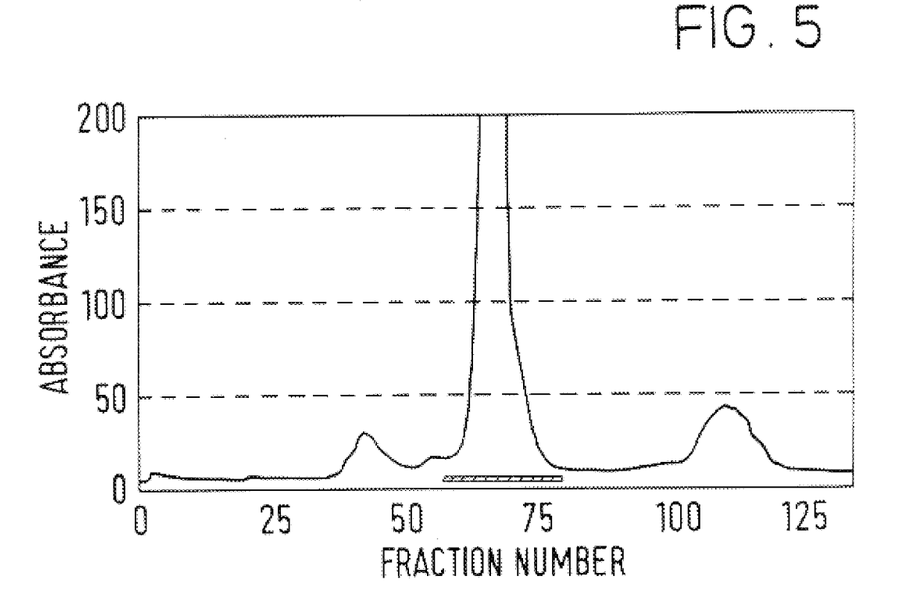
FIG. 5 is a chromatograph of the active fractions obtained from FIG. 4.

By combining similar chromatography steps to those exemplified in Examples 3, 4 and 5, a large batch was prepared. The complete salivary complex of fifty leeches of the species *Haementeria ghilianii* which had not been fed for at least 3 months were homogenised in 20 mM Tris HCl pH8.0 (50 ml) and centrifuged as in Example 1. The supernatant was applied to a 60×10 cm column of Q Sepharose Fast Flow (Pharmacia). Fractions were eluted with a linear gradient from the starting buffer to one containing 0.1M NaCl. The eluate was monitored at 280 nm and the active fraction was found to elute at about 0.09M NaCl (see FIG. 3 in which the fractions containing inhibitory activity are marked with a bar). The active fractions (145 ml) were adjusted to pH 4 by addition of formic acid and applied to a 5×12 cm column of SP Sepharose Fast Flow (Pharmacia) which had been equilibrated in 20 mM. sodium formate buffer pH 3.5. The column was eluted with a linear gradient from the equilibration buffer to the same buffer containing 1M NaCl. The active fraction eluted in a peak at about 0.57M NaCl (see FIG. 4 in which the fractions containing inhibitory activity are again marked with a bar). This was lyophilised and reconstituted in a final volume of 2.4 ml water and applied to a 1.6×60 cm column of Superdex G-75 which had been equilibrated in phosphate-buffered saline pH7.2. The elution profile is shown in FIG. 5 in which the fractions containing inhibitory activity are again marked with a bar. The pooled active fractions contained 715 µg protein and these were stored frozen.

Polyacrylamide gel electrophoresis in sodium dodecyl sulfate and staining with either Coomassie Blue or silver stain demonstrated that the protein was substantially pure after this step and that by comparison with standards of known molecular weight, the major band had an apparent molecular weight of about 7800 daltons with minor bands at higher molecular weight which were only detectable by the more sensitive silver staining method.

EXAMPLE 7

For sequencing work, a further purification step was performed. 0.3 ml of the active fraction from Example 6 was applied to a 0.5×10 cm column of ProRPC equilibrated in 0.1% trifluoroacetic acid and was eluted with a gradient from 0 to 100% acetonitrile containing 0.1% trifluoroacetic acid. A major peak was found which contained the inhibitory activity and this was followed by and widely separated from, two very much smaller, inactive peaks. The active fraction showed a single band on sodium dodecyl sulfate polyacrylamide gel electrophoresis with an apparent molecular weight of about 7800 in comparison with peptidic standards of known molecular weight which are illustrated in FIG. 6.

Figure 6:
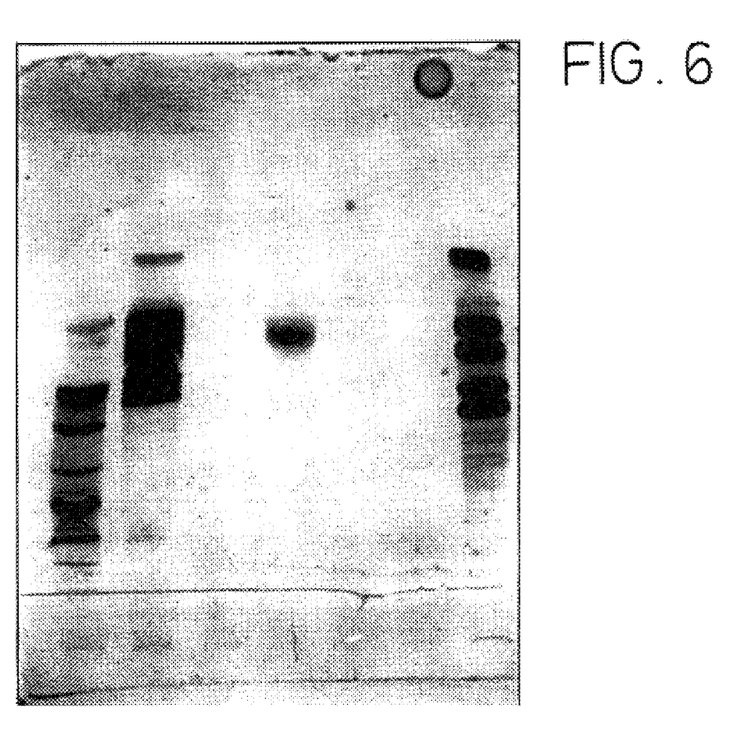
FIG. 6 is an illustration of the results of sodium dodecyl sulfate polyacrylamide gel electrophoresis from Example 7.

FIG. 6 is a polyacrylamide gel electrophoresis in sodium dodecyl sulfate of the pure polypeptide on a PhastGel high density gel (Pharmacia). The left hand lane (lane 1) and lane 7 are low molecular weight marker kit (Pharmacia) of 94, 67, 43, 30, 20.1 and 14.4 kD plus aprotinin (molecular weight 6.5 kD). Lanes 2 and 7: peptide marker kit (Pharmacia) of molecular weights 16.9, 14.4 10.7, 8.2 and 6.2 kD plus aprotinin (6.5 kD). Lane 3: water blank. Lane 4: Purified Tridegin. Lane 5 and 6: minor peaks from reverse phase chromatography column. The lowest molecular weight components migrate nearest the top of the gel.

A single, clean, amino acid sequence was found from the amino terminus by an Applied Biosystems 473A automatic protein sequencer indicating that only one peptide was present. The amino acid sequence was found to be:

NH$_2$-Lys-Leu-Leu-Pro-X-Lys-Glu-Y-His-Gln-Gly-Ile-Pro-Asn-Pro-Argwhere X and Y were not identified positively and therefore could be any amino acid. The cysteines in this sample were not derivatised and therefore could not be assigned. The sequencing was repeated after pyridylethylation and this showed residue X to be a cysteine whereas Y gave no peak at all and could not be assigned to any common amino acid.

EXAMPLE 8

In order to produce enough material for amino acid sequencing, a sample of the transglutaminase inhibitor was prepared from the posterior salivary glands only of fifty leeches of the species *Haementeria ghilianii* by an identical method to that used in Examples 6 and 7. Aliquots were denatured, amidocarboxymethylated and digested by either trypsin or AspN endoprotease by the standard methods described in Matsudaira ("A practical guide to protein and peptide purification for microsequencing" Academic Press. 2nd Edition pp. 45–67), and the fragments were separated on a 0.5×10 cm column of ProRPC equilibrated in 0.06%, trifluoroacetic acid and eluted with sequential linear gradients from 2 to 38%. 38 to 75% and 75 to 98% elution buffer where the elution buffer was 80% acetonitrile in 0.0675% trifluoroacetic acid and monitored at 210 nm. The sequence of the isolated fragments was determined by an Applied Biosystems 473A automatic protein sequencer. The amino acid sequence of the whole polypeptide was deduced from this and the overlapping peptides that were found:

could not be distinguished between Cys or Glu. The polypeptide having this sequence is designated as Tridegin variant 1.

EXAMPLE 9

Besides the assays which demonstrate the ability of factor XIIIa to incorporate amines into casein and the effects of Factor XIIIa on clot solubility, the specificity of the inhibitory action can be shown by an assay which measures the production of ammonia from casein when amines are incorporated. The transglutaminase activity of human plasma factor XIIIa was measured spectrophotometrically by a modification of the method of Muszbek, Polgar and Fesus; "Kinetic determination of blood coagulation factor XIII in plasma." Clin Chem 31 (1985) pp. 35–40. This method measures the production of ammonia by linking it through the glutamate dehydrogenase reaction to NADH oxidation which can be monitored by the change in absorption at 340 nm. Factor XIII was activated by incubating defibrinated human plasma (2 ml) and 200 mM CaCl$_2$ (0.1 ml) with 1000 unit/ml bovine thrombin (0.1 ml) at 37° C. After 15 min the reaction was stopped by the addition of 260 antithrombin units of hirudin. The reaction cuvette contained: 2.5 mM dithiothreitol (0.1 ml), 40 mg/ml dephosphorylated β-casein (0.05 ml), 70 mM ethylamine (0.1 ml), 12 mM sodium 2-ketoglutarate (0.1 ml), 4 mM NADH (0.1 ml), 1.2 mM ADP (0.1 ml), 40 unit/ml glutamate dehydrogenase (0.1 ml), 70 mM HEPES buffer pH7.5 (0.25 ml) and this was placed in a spectrophotometer at 20° C. All components were dissolved in 70 mM HEPES buffer pH 7.5 where possible. The reaction was started by the addition of the activated factor XIII (0.2 ml) and monitored at 340 nm. The assay was validated with the use of factor XIII-deficient plasma (Sigma). Replacement of the normal plasma with the deficient plasma resulted in a rate of reaction that was 88% lower (1.87 versus 11.3 mAbs/min) demonstrating that the assay actually measures factor XIIIa.

Test samples were added in 0.1 ml of the HEPES buffer to the reaction cuvette. The inhibitory effect of Tridegin variant 1 was compared to that of iodoacetamide, a known inhibitor of the sulfhydryl group-dependent factor XIIIa and EGTA, an inhibitor of factor XIII activation and activity by virtue of its chelation of essential calcium as shown in Table 3. The Tridegin lowered the rate of ammonia production by

```
          1                              10
NH2-Lys-Leu-Leu-Pro-Cys-Lys-Glu-X1-His-Gln-Gly-

20
Ile-Pro-Asn-Pro-Arg-Cys-X2-Cys-Gly-Ala-Asp-Leu-

30
Glu-X3-Ala-Gln-Asp-Gln-Tyr-Cys-Ala-Phe-Ile-Pro-

40
Gln-Z1-Arg-Pro-Arg-Ser-Glu-Leu-Ile-Lys-Pro-Met-

50
Asp-Asp-Ile-Tyr-Gln-Arg-Pro-Val-Z2-Phe-Pro-Asn- 60                    66
Leu-Pro-Leu-Lys-Pro-Arg-Z3-COOH
``` wherein amino acids $X_1$, $X_2$ and X3 were not identifiable and may represent residues that have been modified post translationally and $Z_1$, $Z_2$ and $Z_3$ represents amino acids that about 93%, that is the inhibition was equivalent to that of iodoacetamide (as shown in Table 3). This is additional evidence which shows that Tridegins, as well as being inhibitors of clot solubilisation, are inhibitors of plasma transglutaminase or factor XIIIa.

TABLE 3

| Test Sample (concentration in cuvette) | Change in absorbance (mAbs/min) |
|---|---|
| Control | 4.14 |
| EGTA (77 mM) | 0.024 |
| Iodoacetamide (0.077 mM) | 0.356 |
| Tridegin (3.89 µg/ml) | 0.28 |

EXAMPLE 10

The effect of Tridegin variant 1, purified as in Example 6, on the ability of human factor XIIIa to catalyse the incorporation of biotinamidopentylamine into casein was measured by the microtitre plate method described by Slaughter T F, Achyuthan K E, Lai T-Sand Greenberg C S. (1992). ("A microtitre plate transglutaminase assay utilizing 5-(biotinamido)pentylamine as substrate". Anal Biochem 205: 166–171). N,Ndimethylcasein was dissolved in 0.1M Tris HCl pH 8.5 by stirring at 85° C. for 30 min and then centrifugation at 12000 g for 20 min. A concentration of 10–20 mg/ml (0.2 ml) was used to coat the wells of a microtitre plate by incubation at 37° C. for 1 h. The excess casein was discarded and the wells blocked with 0.5% non fat dry milk in 0.1M Tris HCl pH 8.5 for 30 min. The plate was then washed twice with 0.35 ml aliquots of the Tris buffer. Purified human platelet factor XIII (0.6 unit/0.12 ml) was activated by addition of 150 U/ml thrombin in 15 mM $CaCl_2$ (0.18 ml) and incubation at 37° C. for 15 min. The thrombin was then inhibited by addition of 140 ATU/ml natural hirudin (0.3 ml). Nicrotitre plate wells (total volume 0.2 ml) contained 5 mM $CaCl_2$, 10 mM dithiothreitol, 0.5 mM biotinamidopentylamine, Tridegin sample prepared in a similar way to that described in Example 6 and 0.25 unit/ml of the activated factor XIIIa in 0.1M Tris HCl pH 8.5. After incubation at 37° C. for 30 min, the liquid was discarded and the reaction stopped by two washes in 0.2M EDTA (0.35 ml each) followed by two washes with 0.1M Tris HCl pH8.5 (0.35 ml each). 0.25 mg/ml streptavidin-alkaline phosphatase was diluted 1:150 with 0.5% non fat dry milk in the Tris buffer and 0.25 ml was added to each well and incubated for 1 h at 20° C. The plate was washed once with 0.1% Triton X-100 (0.35 ml) followed by 3 washes with the Tris buffer (0.35 ml). Bound alkaline phosphatase was measured by addition of 1 mg/ml p-nitrophenyl phosphate, 5 mM $MgCl_2$ in the Tris buffer (0.05 ml) plus Tris buffer (0.2 ml) and the absorbance measured after 30 min using a Titertek Uniskan II microtitre plate reader at 405 nm.

Tridegin variant 1 clearly inhibited the incorporation of the amine with an IC50 of 0.026±0.002 µg/ml (3.4 nM) confirming its very potent inhibitory activity on platelet factor XIIIa.

In a separate experiment using an identical protocol except replacing the purified factor XIII with plasma from a healthy human volunteer and varying the concentration of the Tridegin, the IC50 was determined to be 0.07±0.003 µg/ml (9.2 nM) for the plasma form of factor XIIIa.

EXAMPLE 11

The effect of Tridegin variant 1 purified as in Example 6 was tested on the coagulation enzyme, thrombin. with a chromogenic substrate assay. 1 mM S2238 was incubated in 50 mM Tris HCl pH 8.3 and the reaction was started by adding thrombin 0.15 U/ml final concentration. The reaction was monitored in a spectrophotometer at 405 nm. Table 4 shows that Tridegin had no effect on thrombin at a concentration of 4.6 µg/ml whereas hirudin at a concentration of 0.046 µg/ml had a marked inhibitory effect (95%).

TABLE 4

| Test Sample | Concentration (µg/ml) | Rate of Reaction (mAbs/min) |
|---|---|---|
| Control | — | 49.8 |
| Tridegin | 4.6 | 51.8 |
| Hirudin | 0.046 | 2.63 |

EXAMPLE 12

The effect of the Tridegin purified as in Example 6 was tested on factor Xa. 2 mM S2765 was incubated in 50 mM Tris HCl pH 8.3 and the reaction was started by adding human factor Xa. The assay was performed as in Example 11. The transglutaminase inhibitor at 4.6 µg/ml had no effect on factor Xa whereas recombinant tick anticoagulant peptide (rTAP), a known inhibitor of factor Xa (Waxman L. Smith D E, Arcuri K et al. "Tick anticoagulant peptide (TAP) is a novel inhibitor of blood coagulation factor Xa" Science 248: 593–596: 1990), inhibited by 89.9% at a concentration of 0.046 µg/ml (Table 5). This confirms that, not only is the transglutaminase inhibitor different from previously known inhibitors of factor Xa, but the methods exemplified to purify the transglutaminase inhibitor successfully remove the factor Xa inhibitors.

TABLE 5

| Test Sample | Concentration (µg/ml) | Reaction Rate (mAbs/min) |
|---|---|---|
| control |  | 49.8 |
| Tridegin | 4.6 | 56.1 |
| rTAP | 0.046 | 5.53 |

EXAMPLE 13

In order to ascertain if Tridegins have a hementin-like fibrinogenolytic activity, the ability of the purified material from Example 6 to direst fibrinogen was evaluated by assessing the clottability of fibrinogen after incubating it with the inhibitor. 2 mg/ml bovine fibrinogen (50 µl) was incubated with the Tridegin, purified hementin or vehicle (50 µl) and 20 mM HEPES buffer containing 10 mM $CaCl_2$ and 0.1% w/v Brij 35 pH 7.5 (50 µl) at 37° C. for 60 min. Then 100 U/ml thrombin (10 µl) was added to cause clotting and the clot was measured by the turbidity at 405 nm after 30 min. Table 6 shows that the transglutaminase inhibitor had no effect on the clot formation whereas purified hementin had clearly digested the fibrinogen and little clot resulted. This indicates that Tridegins have no proteolytic action on fibrinogen and therefore are not hementin as described in WO 91/15576 ("Treatment of thrombotic events") and U.S. Pat. No. 4,390,630, ("Hementin—a fibrinolytic agent"). In addition, this example adds further confirmation that the hementin which is found in *Haementeria ghilianii* is separated from the transglutaminase inhibitor during the purification procedures exemplified.

TABLE 6

| Test Sample | Absorbance | Absorbance |
|---|---|---|
| buffer control | 0.238 | 0.224 |
| Tridegin (35 µg/ml) | 0.226 | — |
| Hementin (30 unit/ml) | — | 0.007 |

EXAMPLE 14

The activity of the enzyme, destabilase, can be measured by its effect in causing the release of p-nitroaniline from the chromogenic substrate, L-γ-glutamyl p-nitroanilide. In order to ascertain whether destabilase and the Tridegins have similar properties, the effect of the two agents on the chromogenic substrate was compared. The absorbance of cuvettes containing 0.45 mg/ml L-γ-glutamyl p-nitroanilide in 50 mM Tris HCl, 10 mM $CaCl_2$ pH 8.0 (0.9 ml) was continuously recorded at 405 nm in a spectrophotometer. Either 0.046 mg/ml Tridegin variant 1 (0.1 ml) or the supernatant from an extract of *Hirudo medicinalis* (0.1 ml), a known source of destabilase, prepared as in Example 2, was added and the rate of generation of nitroaniline measured. Table 7 shows the effect of Tridegin on the destabilase substrate, L-γ-glutamyl p-nitroanilide, and indicates that although *Hirudo medicinalis* extract contains an activity which causes an increase in the rate of absorbance indicating cleavage of this substrate attributable to destabilase, the Tridegin had no such effect and in fact results in a slight decrease in absorbance over time.

TABLE 7

| | Reaction Rate (mAbs/min) |
|---|---|
| *Hirudo medicinalis* extract | 2.04 |
| Tridegin (4.6 µg/ml) | −1.17 |

EXAMPLE 15

Tridegin was tested for its effect on the clotting of plasma by comparing a sample of normal plasma to which had been added 0.1 volumes of of the inhibitor purified as in Example 6 (46 µg/ml) in phosphate-buffered saline with one that had buffer alone. Standard clotting tests were carried out on an automated analyser. The results in Table 8 show that there was no difference in the two samples so Tridegin has no effect on the clotting time of normal human plasma. This property is expected since inhibitors of fibrin cross-linking have no effect on clot formation and only influence its physical and chemical properties after it has formed. Moreover this confirms, in a different test, the absence of any other anticoagulant activity such as inhibition of factor Xa or thrombin in Tridegin.

Platelet aggregation was assessed in human citrated platelet-rich plasma in a Bio/Data aggregometer in response to either 6.7 µg/ml collagen, 6.3 µM ADP or 0.4 U/ml thrombin. Tridegin from Example 6, at a final concentration of 4.6 µg/ml was compared to buffer controls. Table 8 shows that the Tridegin clearly has no effect on platelet aggregation under these conditions.

TABLE 8

| Parameter | Control | Tridegin (4.6 µg/ml) |
|---|---|---|
| Thrombin clotting time (sec) | 9.8 | 9.8 |
| One stage prothrombin time (sec) | 15.2 | 14.7 |
| Kaolin cephalin clotting time (sec) | 28.5 | 27.9 |
| Collagen-induced aggregation (%/min) | 23 | 28 |
| ADP-induced aggregation (%/min) | 11 | 14 |
| Thrombin-induced aggregation (%/min) | 73 | 82 |

EXAMPLE 16

The effect of the inhibitor on guinea pig liver tissue transglutaminase was measured in an assay similar to that described in Example 10 where the activated factor XIIIa was substituted with tissue transglutaminase. Tridegin (4.5 µg/ml) inhibited the incorporation of the amine into casein catalysed by this enzyme by 95.5%. By using different concentrations of Tridegin the IC50 was found to be 1.55 µg/ml. This assay indicates that the Tridegin is an inhibitor of tissue transglutaminase as well as of the plasma transglutaminase factor XIIIa and that it is likely to be an inhibitor of many of the transglutaminase enzymes.

EXAMPLE 17

The transglutaminase inhibitor is measurable in the glands of the salivary system and in salivary secretions of *Haementeria ghilianii* by the amine incorporation assay of Slaughter T F, Achyuthan K E, Lai T-S and Greenberg C S. (1992). ("A microtitre plate transglutaminase assay utilizing 5-(biotinamido)pentylamine as substrate". Anal Biochem 205: pp. 166–171). The anterior and posterior salivary glands and the proboscis together with the hind sucker were removed from a starved third-fed stage animal. The samples were homogenised in a glass homogeniser in 1 mM Tris HCl pH8.0 (1 ml or 0.5 ml in the case of the posterior glands) and centrifuged at 12000 rpm. The supernatant was used for the assay. For collection of the salivary secretion the complete salivary apparatus (proboscis, anterior and posterior glands) of each of eight starved third-fed stage *Haementeria ghilianii* was removed after chilling the leeches at 5° C. for 2–3 h. It was pinned out on to a Sylgard base and bathed in physiological saline solution (65 mM NaCl, 50 mM $NH_4Cl$, 4 mM KCl, 1 mM EGTA, 11 mM glucose, 10 mM HEPES pH 7.4) at 20° C. for 15 min. By cutting the wall of the proboscis longitudinally, the lumen was accessed and secretions contained therein were collected by micropipette.

Table 9 shows the inhibition of human plasma factor XIIIa by these extracts and secretions of the leech *Haementeria ghilianii*. The inhibitory activity is found in both salivary glands, in the salivary secretion and in the proboscis. The very low activity detectable in the hind sucker is of very low specific activity, being 0.35% that in the posterior salivary gland, and in fact the apparent activity detected may well result from the very high protein concentration extracted from this large piece of tissue.

TABLE 9

| Tissue | Specific activity (unit/mg)[#] | % inhibition |
|---|---|---|
| Anterior salivary gland | 19.0 | 99.7 |
| Posterior salivary gland | 93.3 | 100 |

TABLE 9-continued

| Tissue | Specific activity (unit/mg)[#] | % inhibition |
| --- | --- | --- |
| Proboscis | 11.7 | 95.5 |
| Hind sucker | 0.33 | 48.5 |
| Luminal secretion from proboscis* | —[+] | 61.9 |

[#]1 unit is defined as double the amount of transglutaminase inhibitor required to inhibit factor XIIIa in 1 ml normal human plasma by 50% in the amine incorporation assay described in Example 10.
*mean of eight separate experiments.
[+]the protein concentration was too low to measure (the specific activity is very high).

EXAMPLE 18

The potentiating effect of the Tridegin on fibrinolysis induced by plasmin was demonstrated by an absorbance method. 10 mg/ml bovine fibrinogen (0.1 ml) was incubated with 50 U/ml bovine thrombin (0.01 ml) with either buffer or Tridegin from Example 6 (0.04 ml) for 2 h at 37° C. in a microtitre plate. 2.56 U/ml plasmin (0.05 ml) was added and the plate was incubated at 37° C. The absorbance was measured every 15 min on a Titretek Uniskan II microtitre plate reader. The clot was viewed every 15 minutes and the time taken for the clot to completely dissolve was recorded. At all the concentrations tested, the transglutaminase inhibitor shortened the time for lysis to occur as illustrated in Table 10.

TABLE 10

| [Tridegin] (µg/ml) | Time for lysis (h) |
| --- | --- |
| 0 | 3.0 |
| 2.0 | 1.0 |
| 1.0 | 1.25 |
| 0.2 | 1.25 |
| 0.1 | 2.5 |
| 0.04 | 1.5 |

EXAMPLE 19

The accelerating effect of Tridegin on fibrinolysis induced by tissue plasminogen activator was also shown on human plasma clots. Human plasma (0.1 ml) was incubated with 5 U/ml bovine thrombin in 0.18M CaCl, containing 0.14M KCl (0.01 ml) and either buffer or Tridegin prepared as in Example 6 but from the posterior salivary glands of *Haementeria ghilianii* (0.04 ml) for 2 h at 37° C. in a microtitre plate in replicates of six. Tissue plasminogen activator (0.05 ml) was then added to a final concentration of 10 IU/ml and the plate was incubated at 37° C. and absorbance readings were taken every 30 min at 405 nm using a Titretek Uniskan II microtitre plate reader. The reduction in absorbance indicated lysis of the plasma clots. The time taken for 50% lysis in the control wells was 12.9±1.1 h and in the wells containing the transglutaminase inhibitor, 7.9±0.7 h, a statistically significant reduction. This example confirms that the transglutaminase inhibitor dramatically accelerates the action of tissue plasminogen activator on human plasma clots.

EXAMPLE 20

Singe platelets invariably become associated with thrombi in vivo, it is of interest to see if the transglutaminase inhibitors allow more rapid lysis of platelet-rich clots, a more physiological test. Platelets are a rich source of the plasma transglutaminase, factor XIII, as well as inhibitors of fibrinolysis so they severely reduce the efficacy of fibrinolytic agents. Human platelet-rich or platelet-poor plasma prepared from the same donor (0.1 ml) was incubated with 5 U/ml bovine thrombin in 0.18M $CaCl_2$ containing 0.14M KCl (0.01 ml) and either buffer or Tridegin (prepared as in Example 6 but from the posterior salivary glands of the species *Haementeria ghilianii*, 0.04 ml) for 2 h at 37° C. in a microtitre plate in replicates of six. Tissue plasminogen activator (0.05 ml) was added to a final concentration of 10 IU/ml and the plate incubated at 37° C. Absorbance readings were taken every 30 min for 72 h at 405 nm using a Molecular Devices Thermomax kinetic microtitre plate reader (lowered absorbance showing lysis of plasma clots). Table 11 shows that in the presence of platelets the clots did not achieve 50% lysis in a 72 hour incubation period. Tridegin is even more effective at reducing the effect of platelets when present as it reduces the time from >72 h to 24.9 h in their presence and from 2.5 h to 18.0 h in their absence in this Example.

TABLE 11

|  | control buffer (time for 50% lysis in hours) | Tridegin (time for 50% lysis in hours |
| --- | --- | --- |
| Platelet-poor plasma | 22.5 ± 1.99 | 18.0 ± 1.03 |
| Platelet-rich plasma | >72 | 24.9 ± 5.57 |

EXAMPLE 21

Figure 7:
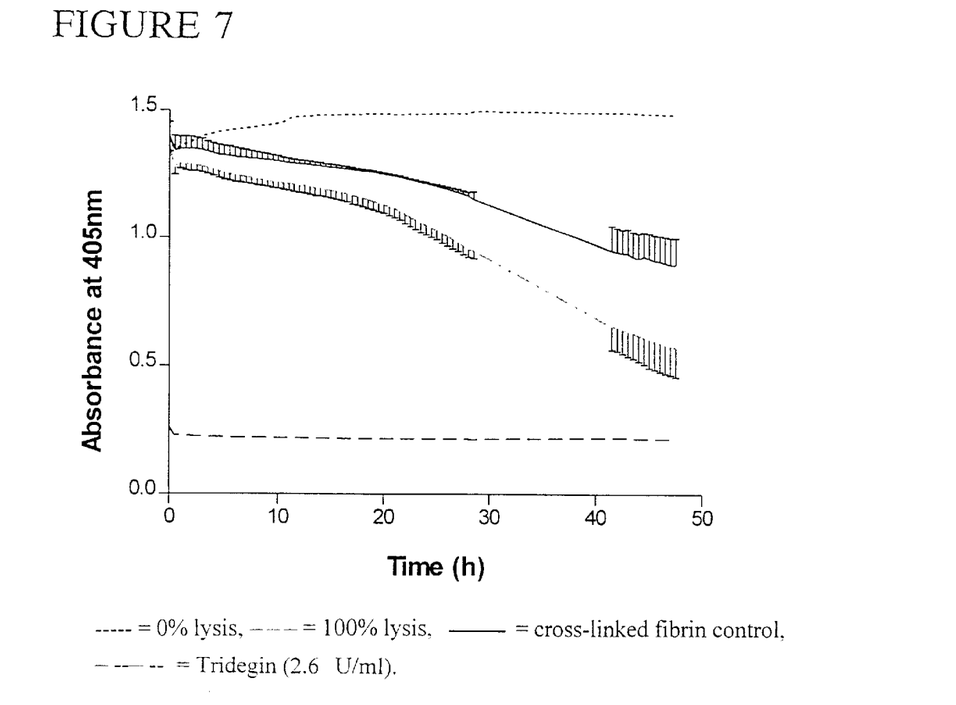
FIG. 7 is an illustration of the results obtained from Example 22.

The effect of Tridegin to decrease clot lysis times is a general effect and can be shown when streptokinase is used as the lytic agent. Human plasma (0.1 ml) was incubated with 5 U/ml bovine thrombin in 0.18M $CaCl_2$ containing 0.14M KCl (0.01 ml) and either buffer or Tridegin prepared as in Example 6 but from the posterior salivary lands of *Haementeria ghilianii* (0.04 ml) for 2 h at 37° C. in a microtitre plate in triplicate. Streptokinase was then added to a final concentration of 30 U/ml and the plate was incubated in an iEMS kinetic microtitre plate reader at 37° C. and absorbance readings were taken every 30 min for 47.5 h at 405 nm. Although the wells containing streptokinase alone had not lysed sufficiently to obtain a time for 50% lysis, all the wells that contained the Tridegin lysed by 50% in 36.1±1.6 h demonstrating again the accelerating effect when used in combination with fibrinolytic agents like streptokinase is shown in FIG. 7 (which shows the effect of Tridegin on plasma clot lysis induced by streptokinase). The results are ±SEM (n=3).

EXAMPLE 22

The combination of Tridegin and hementin was investigated as described in Example 21, where the tissue plasminogen activator was replaced with 110 U/ml hementin. In this Example both platelet-free and platelet-rich plasma samples from the same donor were used in order to ascertain if there was an difference. Table 12 shows the times taken for 50% lysis to occur in the samples. There is a clear effect of platelets which increase the time required for lysis from 34 h to >56 h yet clearly the Tridegin reduces the time for 50% lysis to occur whether platelets are absent or present. The Tridegin seems to largely overcome the effect of the platelets by decreasing the lysis time close to that of the control.

TABLE 12

|  | Buffer (time for 50% lysis in hours) | Tridegin (time for 50% lysis in hours) |
|---|---|---|
| Platelet-free plasma | 34 ± 3.5 | 24 ± 0.8 |
| Platelet-rich plasma | >56 ± 7.8 | 36 ± 2.2 |

EXAMPLE 23

Figure 8:
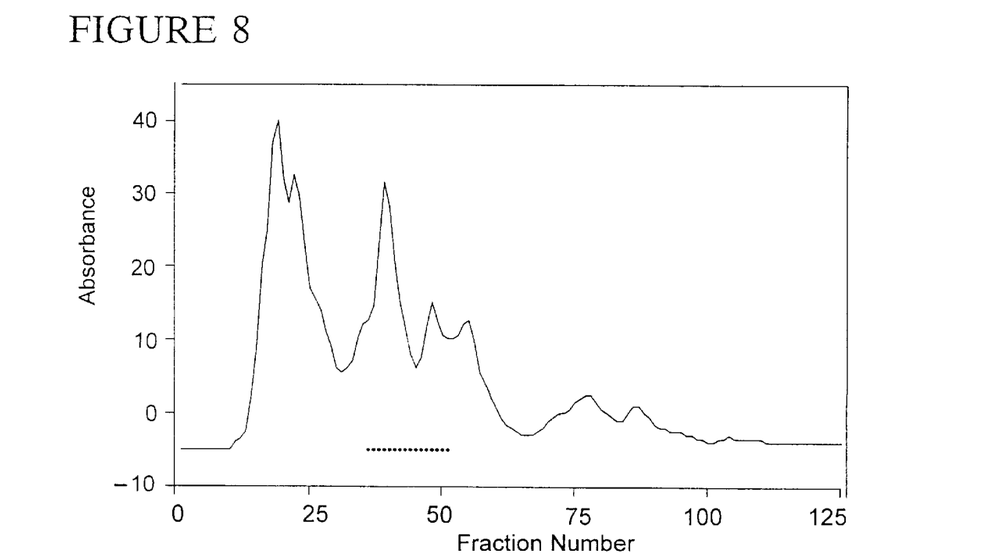
FIG. 8 is an illustration of the results obtained from Example 24.

In order to investigate the properties of Tridegin derived from the Mexican leech. *Haementeria officinalis*, an extract was chromatographed on gel filtration followed by reverse phase high pressure liquid chromatography. The salivary glands and probosces were dissected from five specimens of *Haementeria officinalis* that had been starved to a point where no blood was found in the foregut. These were homogenised in phosphate buffered saline pH 7.2 (1 ml) in a Teflon/glass homogeniser and centrifuged at 12000 g for five minutes in order to obtain a clear supernatant. The supernatant was applied to a 1.6×60 cm column of Superdex G75 and the eluate was monitored at 280 nm and all fractions were collected and assayed in a clot solubility assay as in Example 1. The inhibitory activity was found in a single peak as indicated in FIG. 8 (in which again the fractions containing the inhibitory activity are marked with a bar).

The active fraction was lyophilised and redissolved in water (1 ml). Part of this (0.3 ml) was applied to a 0.5×10 cm column of Pro-RPC which had been equilibrated in 0.1% trifluoroacetic acid (TFA). Elution with a linear gradient of 0.1% TFA to acetonitrile containing 0.1% TFA resulted in the elution of a large number of peaks which absorbed at 280 nm. Each was assayed in the clot solubility assay as described in Example 1 and a single peak was found to contain activity.

Comparison of the elution positions on the two columns with that for similar extracts of *Haementeria ghilianii* indicated the close similarity with the elution position of Tridegin variant 1. The inhibitory activity purified from the salivary glands of *Haementeria officinalis* has very similar physicochemical properties in terms of molecular weight, as determined by gel filtration, and partition coefficient, as determined by reverse phase high pressure liquid chromatography to those of Tridegin variant 1.

EXAMPLE 24

To determine the behaviour of Tridegin variant 1 in vivo, a dose of 0.207 mg/kg i.v. formulated in 0.01M sodium phosphate, 0.027M KCl, 0.137M NaCl pH 7.4 (4.7 ml) was administered intravenously to a group of four rats. Blood samples (approx. 0.3 ml) were taken from the tail vein both before and 2 or 5 and 10, 20, 30, 60 and 120 minutes after administration and mixed immediately with 0.04 ml 3.8% w/v trisodium citrate. The samples were immediately centrifuged at 12000 g for 5 min and the supernatants removed and flash frozen on dry ice. No side effects of the Tridegin administration were noted.

The Tridegin in the samples was assayed by a modification of the amine incorporation assay used in Example 2 where the intrinsic factor XIII was activated in each sample (0.097 ml) by addition of 0.1M Tris HCl pH 8.5 (0.03 ml) and 1000 U/ml bovine thrombin (0.01 ml) and incubation at 37° C. for 15 minutes. The fibrin clot was removed by centrifugation and the serum used for the assay. Samples for the standard curve were prepared by addition of known concentrations of pure Tridegin variant 1 to citrated rat plasma and activation of the factor XIIIa in an identical way. The Tridegin concentration in each sample was then determined by the percentage inhibition of the factor XIIIa as in Example 2 by comparison with the standard curve.

Figure 9:
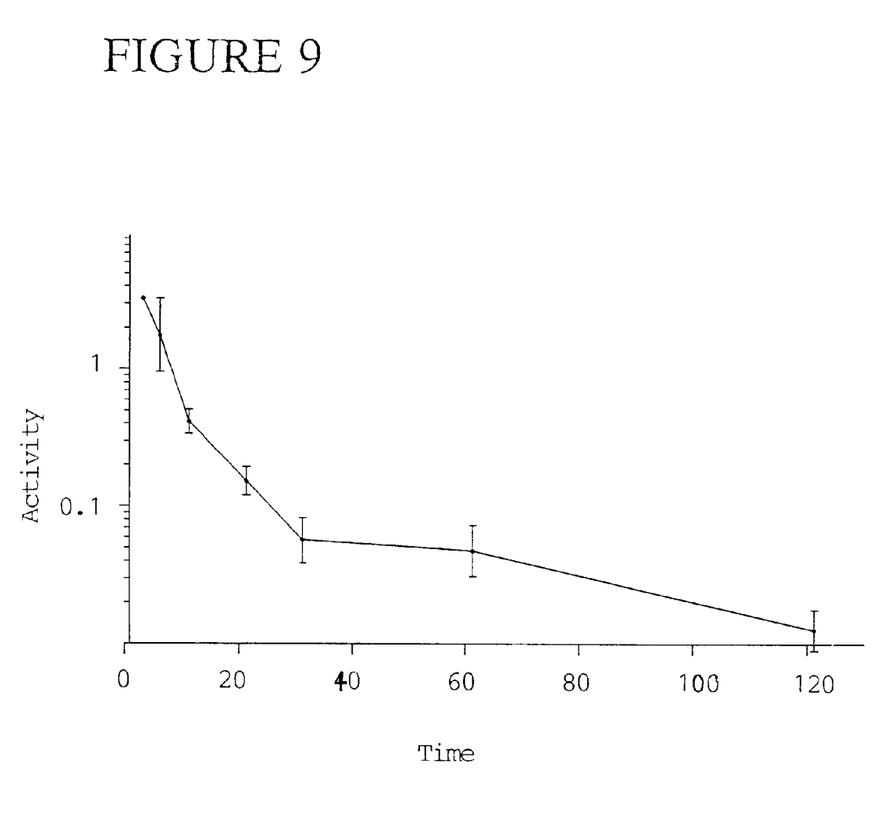
FIG. 9 is an illustration of the results obtained from Example 25.

FIG. 9 shows Tridegin's pharmacokinetics in the rat. The time course is clearly multiphasic: the terminal half life is 30–60 minutes indicating significant duration of action and that Tridegin's pharmacokinetics make it suitable for pharmaceutical use.

We claim:

1. A polypeptide having the following amino acid sequence

NH$_2$-Lys-Leu-Leu-Pro-Cys-Lys-Glu-Y-His-Gln-Gly-Ile-Pro-Asn-Pro-Argwherein Y represents any amino acid residue; or a pharmaceutically acceptable salt, or truncated form thereof of substantially similar activity (sequence ID No: 1).

2. A polypeptide having the following amino acid sequence,

```
       1                             10
NH2-Lys-Leu-Pro-Cys-Lys-Glu-X1-His-Gln-Gly-

20
Ile-Pro-Asn-Pro-Arg-Cys-X2-Cys-Gly-Ala-Asp-Leu-

30
Glu-X3-Ala-Gln-Asp-Gln-Tyr-Cys-Ala-Phe-Ile-Pro-

40
Gln-Z1-Arg-Pro-Arg-Ser-Glu-Leu-Ile-Lys-Pro-Met-

50
Asp-Asp-Ile-Tyr-Gln-Arg-Pro-Val-Z2-Phe-Pro-Asn- 60                            66
Leu-Pro-Leu-Lys-Pro-Arg-Z3-COOH  (Sequence ID NO:2)
``` wherein $X_1$, $X_2$ and $X_3$ each represent any amino acid residue; $Z_1$, $Z_2$ and $Z_3$ each represent, simultaneously or alternatively Cys or Glu; or a pharmaceutically acceptable salt, or a truncated form thereof of substantially similar activity.

3. A polypeptide according to claim 1, which is obtained from leech tissue or secretions.

4. A polypeptide according to claim 3, wherein the leech is of the order Rhynchobdellida.

5. A polypeptide according to claim 1, which is obtained from the tissue or secretions of leeches of the genus Haementeria.

6. A transglutaminase inhibitor, which is obtained from leech tissue or leech secretions.

7. A transglutaminase inhibitor according to claim 6, wherein the leeches are of the order Rhynchobdellida.

8. A transglutaminase according to claim 7, wherein the leeches are of the genus Haementeria.

9. A transglutaminase inhibitor according to claim 6, wherein said inhibitor is a polypeptide with an apparent molecular weight of approximately 7000 to 8000 daltons as measured by polyacrylamide gel electrophoresis.

10. A transglutaminase according to claim 6, wherein said inhibitor has the ability to inhibit the factor XIIIa catalysed incorporation of amines into casein.

11. A transglutaminase according to claim 6, wherein said inhibitor has the ability to inhibit the factor XIIIa catalysed incorporation of biotinamidopentylamine into casein with an IC50 0.026±0.002 mg/ml.

12. A diagnostic method for measuring the degree of inhibition of transglutaminase activity for a polypeptide according to claim 1 or a transglutaminase inhibitor according to claim 6, which method comprises measuring the amount of ammonia liberated from the transglutaminase catalysed incorporation of amines into casein in the presence of said polypeptide or said inhibitor, respectively, wherein the amount of ammonia liberated provides a measure of the level of inhibition of the transglutaminase.

13. A pharmaceutical formulation comprising a polypeptide according to claim 1, and/or a transglutaminase inhibitor according to claim 6, and a pharmaceutically acceptable carrier, diluent or excipient therefore.

14. A pharmaceutical formulation according to claim 13, for administration in combination with an anticoagulant.

15. A pharmaceutical formulation according to claim 14, wherein the anticoagulant comprises hirudin or heparin.

16. A pharmaceutical formulation according to claim 13, for administration in combination with a fibrinolytic, fibrinogenolytic or thrombolytic agent.

17. A pharmaceutical formulation according to claim 16, wherein the thrombolytic agent comprises one or more of tissue plasminogen activator, plasmin, streptokinase, eminase, urokinase, hementin and staphlyokinase.

18. A pharmaceutical formulation according to claim 16, wherein the fibrinolytic or fibrinogenolytic agent comprises hementin.

19. A process for the isolation of a polypeptide according to claim 1 or a transglutaminase inhibitor according to claim 6, which process comprises extracting tissue or secretions of leeches of the order Rhynchobdellida and purifying the extracted material by one or more of ion-exchange column chromatography, gel filtration column chromatography and reverse phase chromatography.

20. A transglutaminase inhibitor which is obtained from leech tissue or secretions, wherein said inhibitor is a polypeptide with an apparent molecular weight of approximately 7000 to 8000 daltons as measured by polyacrylamide gel electrophoresis.

* * * * *